(12) United States Patent
Mittal

(10) Patent No.: US 9,655,856 B2
(45) Date of Patent: May 23, 2017

(54) SOLID PHARMACEUTICAL COMPOSITIONS AND PROCESSES FOR THEIR PRODUCTION

(71) Applicant: Millennium Pharmaceuticals, Inc., Cambridge, MA (US)

(72) Inventor: Bhavishya Mittal, Weymouth, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/860,829

(22) Filed: Sep. 22, 2015

(65) Prior Publication Data

US 2016/0199382 A1     Jul. 14, 2016

Related U.S. Application Data

(62) Division of application No. 12/780,015, filed on May 14, 2010, now Pat. No. 9,173,846.

(60) Provisional application No. 61/268,438, filed on Jun. 12, 2009, provisional application No. 61/216,493, filed on May 18, 2009.

(51) Int. Cl.
| | | |
|---|---|---|
| *A61K 9/16* | (2006.01) | |
| *A61P 35/00* | (2006.01) | |
| *A61K 31/55* | (2006.01) | |
| *A61K 9/20* | (2006.01) | |
| *A61J 3/07* | (2006.01) | |
| *A61K 9/28* | (2006.01) | |
| *A61K 9/48* | (2006.01) | |

(52) U.S. Cl.
CPC .............. *A61K 9/2054* (2013.01); *A61J 3/07* (2013.01); *A61K 9/1652* (2013.01); *A61K 9/1682* (2013.01); *A61K 9/2095* (2013.01); *A61K 9/2846* (2013.01); *A61K 9/2893* (2013.01); *A61K 9/4833* (2013.01); *A61K 31/55* (2013.01)

(58) Field of Classification Search
None
See application file for complete search history.

(56) References Cited

U.S. PATENT DOCUMENTS

| | | |
|---|---|---|
| 5,747,487 A | 5/1998 | Albright et al. |
| 7,572,784 B2 | 8/2009 | Claiborne et al. |
| 8,026,246 B2 | 9/2011 | Claiborne et al. |
| 9,173,846 B2 | 11/2015 | Mittal |
| 2004/0234608 A1 | 11/2004 | Fleshner-Barak et al. |
| 2005/0244490 A1 | 11/2005 | Otto et al. |
| 2005/0256102 A1 | 11/2005 | Claiborne et al. |
| 2007/0104785 A1 | 5/2007 | Navale et al. |
| 2007/0185087 A1 | 8/2007 | Claiborne et al. |
| 2007/0238716 A1 | 10/2007 | Murthy et al. |
| 2008/0045501 A1 | 2/2008 | Claiborne et al. |
| 2008/0167292 A1 | 7/2008 | Claiborne et al. |
| 2009/0299060 A1 | 12/2009 | Claiborne et al. |

FOREIGN PATENT DOCUMENTS

| | | |
|---|---|---|
| JP | 2004-533999 A | 11/2004 |
| JP | 2007-522217 A | 8/2007 |
| JP | 2007-537268 A | 12/2007 |
| TW | 200829589 A | 7/2008 |
| WO | WO-02/072073 A2 | 9/2002 |
| WO | WO-2005/076987 A2 | 8/2005 |
| WO | WO-2005/111039 A3 | 4/2006 |
| WO | WO-2007/080601 A1 | 7/2007 |
| WO | WO-2008/054808 A2 | 5/2008 |
| WO | WO-2008/063525 A1 | 5/2008 |
| WO | WO-2008/118331 A2 | 10/2008 |
| WO | WO-2009/070652 A1 | 6/2009 |
| WO | WO-2009/158687 A1 | 12/2009 |

OTHER PUBLICATIONS

U.S. Appl. No. 61/306,047, filed Feb. 19, 2010, McCubbin et al.
U.S. Appl. No. 12/844,920, filed Jul. 28, 2010, Ramanan et al.
U.S. Appl. No. 13/217,659, filed Aug. 25, 2011, Claiborne et al.
Faure, A. et al., Process Control and Scale-up of Pharmaceutical Wet Granulation Processes: A Review, European Journal of Pharmaceutics and Biopharmaceutics, 52(3):269-277 (2001).
International Search Report for PCT/US2010/001434, 4 pages (Jul. 30, 2010).
International Search Report for PCT/US2010/002109, 4 pages (Jul. 10, 2010).
International Search Report for PCT/US2011/024883, 2 pages (Apr. 11, 2011).
Written Opinion for PCT/US2010/001434, 5 pages (Jul. 30, 2010).

*Primary Examiner* — H. Sarah Park
(74) *Attorney, Agent, or Firm* — Choate, Hall & Stewart LLP; Kristin C. Buteau; Gang Wang

(57) ABSTRACT

This invention provides novel solid pharmaceutical compositions and processes for the bulk production of said compositions. This invention also provides methods of using the pharmaceutical compositions in the treatment of cancer.

24 Claims, No Drawings

SOLID PHARMACEUTICAL COMPOSITIONS AND PROCESSES FOR THEIR PRODUCTION

PRIORITY CLAIM

This application is a divisional of U.S. patent application Ser. No. 12/780,015, filed on May 14, 2010 and issued as U.S. Pat. No. 9,173,846 on Nov. 3, 2015, which claims priority from U.S. Provisional Patent Application Ser. No. 61/216,493, filed on May 18, 2009 and U.S. Provisional Patent Application Ser. No. 61/268,438, filed on Jun. 12, 2009, each of which is hereby incorporated by reference in its entirety.

BACKGROUND OF THE INVENTION

Field of the Invention

This invention relates to novel solid pharmaceutical compositions and processes for the bulk production of said compositions. This invention also provides methods of using the pharmaceutical compositions in the treatment of cancer.

Background of the Invention

In general, solid pharmaceutical compositions comprise a pharmaceutically active ingredient, such as a small molecule, admixed with pharmaceutically acceptable excipients in amounts appropriate to maintain the original activity of the active ingredient. These compositions are typically delivered to patients in the form of tablets or capsules.

Examples of particular active ingredients can be found in U.S. Pat. No. 7,572,784, US Publication No. 2008/0045501, US Publication No. 2008/0167292, and U.S. Application No. 61/306,047, filed Feb. 19, 2010, hereby incorporated by reference in their entirety, which disclose compounds that inhibit Aurora kinase enzymes. These applications additionally disclose methods for the preparation of these compounds, pharmaceutical compositions containing these compounds, and methods for the prophylaxis and therapy of diseases, disorders, or conditions associated with overexpression and/or amplification of Aurora kinases, including, but not limited to, cell proliferative disorders such as cancer.

Important considerations during the manufacturing of solid pharmaceutical compositions include preserving the crystal form of the active ingredient and maintaining the active ingredient's chemical and physical stability. Manufacturers generally target a 2- to 3-year shelf life for pharmaceutical compositions.

Thus, there is a need to develop solid pharmaceutical compositions that are stable and have favorable bioavailability. In particular, there is a need for solid pharmaceutical compositions comprising Aurora kinase inhibitors.

DESCRIPTION OF THE INVENTION

The present invention provides methods for preparing the solid pharmaceutical compositions described herein. These methods offer an alternate approach to processing wet granulation based formulations that require a buffer for bioavailability as compared to prior art methods. It has been determined that the order of addition of excipients during the granulation process affects the drug product's dissolution when stored for stability studies.

In another aspect, the invention provides pharmaceutical compositions that may be prepared by such methods, comprising the active ingredients, buffers and additional excipients as described herein.

In yet another aspect, the invention provides methods for treating disorders using the pharmaceutical compositions as described herein.

The patent and/or scientific literature referred to herein establishes knowledge that is available to those with skill in the art. Unless otherwise defined, all technical and scientific terms used herein have the same meaning as commonly understood by one of ordinary skill in the art to which this invention relates. Although methods and materials similar or equivalent to those described herein can be used in the practice or testing of the present invention, the preferred methods and materials are described herein. The issued patents, applications, and references that are cited herein are hereby incorporated by reference to the same extent as if each was specifically and individually indicated to be incorporated by reference. In the case of inconsistencies, the present disclosure, including definitions, will control. In addition, the materials, methods, and examples are illustrative only and are not intended to be limiting.

DEFINITIONS

The term "active ingredient" is used herein to mean a component of a pharmaceutical composition that is pharmaceutically or physiologically active.

The term "pharmaceutically acceptable excipient" is used herein to refer to a material that is compatible with a recipient subject, preferably a mammal, more preferably a human, and is suitable for delivering an active agent to the target site without terminating the activity of the agent. The toxicity or adverse effects, if any, associated with the excipient preferably are commensurate with a reasonable risk/benefit ratio for the intended use of the active ingredient. Classes of pharmaceutically acceptable excipients include, but are not limited to, surfactants, binders, disintegrants, lubricants, glidants, fillers, and buffers.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

As used herein, "w/w %" is used to mean by weight as a percentage of a total weight that is used as the basis for calculating the weight percentage of an individual component. By way of example, for a bulk composition, the w/w % of an individual component may be calculated as a percentage of the total weight of all of the components of the bulk composition. By way of another example, for a single oral dosage form, the w/w % of an individual component may be calculated as a percentage of the total weight of all of the components of the single oral dosage form. For example, when the single oral dosage form is a coated tablet, the total weight may be the total weight of all the components of the coated tablet including the coating(s). Alternatively, the total weight may be the total weight of all the components of the tablet not including the coating(s)

As used herein, the term "comprises" means "includes, but is not limited to."

As used herein, a "subject" is preferably a bird or mammal, such as a human, but can also be an animal in need of veterinary treatment, e.g., domestic animals (e.g., dogs, cats, and the like), farm animals (e.g., cows, sheep, fowl, pigs, horses, and the like) and laboratory animals (e.g., rats, mice, guinea pigs, and the like).

As used herein, "treating" or "treatment" means prevention, partial alleviation, or cure of a disease, disorder or condition.

As used herein, "therapeutically effective amount" is meant to describe an amount of a compound, composition, medicament or other active ingredient effective in producing the desired therapeutic effect.

As used herein, the term "Aurora kinase" refers to any one of a family of related serine/threonine kinases involved in mitotic progression. A variety of cellular proteins that play a role in cell division are substrates for phosphorylation by Aurora kinase enzymes, including, without limitation, histone H3, p 53, CENP-A, myosin II regulatory light chain, protein phosphatase-1, TPX-2, INCENP, survivin, topoisomerase II alpha, vimentin, MBD-3, MgcRacGAP, desmin, Ajuba, XIEg5 (in *Xenopus*), Ndc10p (in budding yeast), and D-TACC (in *Drosophila*). Aurora kinase enzymes also are themselves substrates for autophosphorylation, e.g., at Thr288. Unless otherwise indicated by context, the term "Aurora kinase" is meant to refer to any Aurora kinase protein from any species, including, without limitation, Aurora A, Aurora B, and Aurora C, preferably Aurora A or B. Preferably, the Aurora kinase is a human Aurora kinase.

The term "Aurora kinase inhibitor" or "inhibitor of Aurora kinase" is used to signify a compound having a structure as defined herein, which is capable of interacting with an Aurora kinase and inhibiting its enzymatic activity. Inhibiting Aurora kinase enzymatic activity means reducing the ability of an Aurora kinase to phosphorylate a substrate peptide or protein. In various embodiments, such reduction of Aurora kinase activity is at least about 50%, at least about 75%, at least about 90%, at least about 95%, or at least about 99%. In various embodiments, the concentration of Aurora kinase inhibitor required to reduce an Aurora kinase enzymatic activity is less than about 1 µM, less than about 500 nM, less than about 100 nM, or less than about 50 nM.

DETAILED DESCRIPTION OF THE INVENTION

In one aspect, the present invention provides methods of preparing a pharmaceutical composition comprising the steps of:
- (a-1) wet granulating at least one active ingredient, and optionally one or more pharmaceutically acceptable excipients independently selected from the group consisting of surfactants, binders, and disintegrants in the presence of a suitable solvent to form a wet mixture;
- (a-2) drying the wet mixture from step (a-1), to form dried granules;
- (a-3) milling the dried granules from step (a-2), to form milled granules; and
- (a-4) blending the milled granules from step (a-3) with a buffer and optionally one or more pharmaceutically acceptable excipients independently selected from the group consisting of surfactants, binders, disintegrants, lubricants and glidants;

wherein a filler is added during step (a-1), during step (a-4), or during both steps (a-1) and (a-4).

In a further embodiment, the methods of the invention also comprise the step of (b-1) loading the resulting mixture from step (a-4) into a capsule.

In another further embodiment, the methods of the invention comprise the step of (c-1) tabletting the resulting mixture from step (a-4) to form a tablet. In some embodiments, the methods of the invention comprise adding a lubricant during step (a-4), and then (c-1) tableting the resulting mixture from step (a-4) to form a tablet.

In still a further embodiment, the methods of the invention also comprise the step of (c-2) coating the tablet resulting from step (c-1). In some embodiments, the tablets are film-coated, or enterically coated, or both. In some other embodiments, the tablets are film-coated and enterically coated.

In a further embodiment, the wet granulating step (a-1) of the methods of the invention is preceded by step (a-0) dry blending at least one active ingredient, and optionally one or more pharmaceutically acceptable excipients independently selected from the group consisting of surfactants, binders, disintegrants, and fillers.

In some embodiments, step (a-4) can be performed as a single blending step during which all of the pharmaceutically acceptable excipients are added at one time. In other embodiments, step (a-4) can be performed as consecutive blending steps during which one pharmaceutically acceptable excipient is added at a time. In still other embodiments, during step (a-4), one or more lubricants may be added after all the other pharmaceutically acceptable excipients have been added.

The wet granulating step (a-1) outlined herein can take place in any conventional granulation system or apparatus. Examples of such granulation equipment include, but are not limited to, high shear granulators, fluid bed granulators, hot melt granulators, one-pot based granulators, extrusion-based granulators, spheronization-based granulators, and spray drying based granulators. An example of a high shear granulator is Diosna P1-6 high shear granulator, which is manufactured by DIOSNA Dierks & Sohne GmbH, Germany. An example of a fluid bed granulator is GPCG-1 batch fluid bed granulator by Glatt Air Techniques, Inc., USA.

In some embodiments, the wet granulating step (a-1) takes between about 5 minutes to about 60 minutes. In some embodiments at least one active ingredient, and optionally one or more pharmaceutically acceptable excipients independently selected from the group consisting of surfactants, binders, and disintegrants are mixed together while a suitable solvent is introduced into the granulation system to form a wet mixture. In some other embodiments, the wet granulating step optionally includes additional mixing time after the suitable solvent has been introduced into the granulation system to achieve a desired granulation end point. In some embodiments, the additional mixing time occurs for less than about 15 minutes, or less than about 10 minutes, or less than about 5 minutes. In some embodiments, the additional mixing time occurs for between about 1 minute to about 5 minutes, or between about 1 minute to about 4 minutes, or between about 1 minute to about 3 minutes, or between about 1 minute to about 2 minutes. In some embodiments, the additional mixing time occurs for about 1 minute, or about 2 minutes, or about 3 minutes, or about 4 minutes, or about 5 minutes.

In some embodiments, the moisture content during the wet granulating step is between about 15% w/w to about 45% w/w, wherein the total weight equals the total amount of material in the wet granulating step. In some embodiments, the moisture content during wet granulating step is between about 20% w/w to about 40% w/w, or between about 25% w/w to about 35% w/w, or about 30% w/w, wherein the total weight equals the total amount of material in the wet granulating step. In some other embodiments, the moisture content during the wet granulating step is about 15% w/w, or about 20% w/w, or about 25% w/w, or about 30% w/w, or about 35% w/w, or about 40% w/w, wherein the total weight equals the total amount of material in the wet granulating step.

The drying step (a-2) outlined herein can take place in any conventional drying system or apparatus. Examples of such drying equipment include, but are not limited to, fluid bed granulators, and equipment for tray drying, microwave drying, and vacuum drying. An example of a fluid bed granulator is GPCG-1, which is manufactured by Glatt Air Techniques, Ramsey, N.J. In some embodiments, the drying step takes between about 5 minutes to about 240 minutes. In some other embodiments, the drying step takes between about 60 minutes to about 240 minutes, or about 180 minutes to about 240 minutes. In some embodiments the inlet air temperature is between about 40° C. to about 85° C. In some other embodiments the inlet air temperature is between about 50° C. to about 80° C., or between about 60° C. to about 75° C., or about 70° C.

The milling step (a-3) outlined herein can take place in any conventional milling system or apparatus. Examples of such milling equipment include, but are not limited to, Comil® U3 (Quadro Engineering LP, Waterloo, ON, Canada), FitzMill® (Fitzpatrick Co., Elmhurst, Ill.) and equipment for screening using sieves. In some embodiments, the milling step takes between about 2 minutes to about 60 minutes.

The blending step (a-4) outlined herein can take place in any conventional blender such as V-blenders, intermediate bulk containers (IBC), drum blenders, tote blenders, cross-flow blenders, and other conventional blenders. An example of a conventional blender is a PK blender, which is manufactured by Patterson-Kelley Co., East Stroudsburg, Pa. In some embodiments, the blending step takes between about 5 minutes to about 120 minutes. In some embodiments, the blending speed is between about 10 rpm to about 60 rpm.

The dry blending step (a-0) outlined herein can take place in any conventional blender such as V-blenders, intermediate bulk containers (IBC), drum blenders, tote blenders, cross-flow blenders, and other conventional blenders. An example of a conventional blender is a PK blender, which is manufactured by Patterson-Kelley Co., East Stroudsburg, Pa. In some embodiments, the blending step takes between about 5 minutes to about 120 minutes. In some embodiments, the blending speed is between about 10 rpm to about 60 rpm.

The capsule loading step (b-1) outlined herein can take place in any conventional capsule filling system or apparatus. In some embodiments, the capsule filling system is semi-automated, and can handle small batch sizes. An example of such a capsule filling system is sold as In-Cap (Isopak Limited, Lincolnshire, Stamford, United Kingdom). In some embodiments, the capsule filling system is manual. An example of such a capsule filling apparatus is sold as ProFill 100 (Torpac, Inc., Fairfield, N.J., USA). An example of a commercial scale encapsulator is a Zanasi 70C, an intermittent motion capsule filler, which is manufactured by I.M.A. Industria Macchine Automatiche S.p.A., Castenaso, Italy.

The tabletting step (c-1) outlined herein can take place in any conventional tablet press. An example of tabletting equipment is the Piccola PLC 8 station PK blender, which is manufactured by SMI Inc, Lebanon, N.J. In some embodiments, the tabletting speed is between about 10 rpm to about 100 rpm.

The coating step (c-2) outlined herein can take place in any conventional tablet coating system. An example of conventional tablet coating equipment is sold as Labcoat I (O'Hara Technologies, Inc, Richmond Hill, ON, Canada). In some embodiments, the coating speed is between about 10 rpm to about 100 rpm. In some embodiments, the coating spray rate is between about 5 g/minute to about 100 g/minute.

Suitable fillers include, but are not limited to, lactose, microcrystalline cellulose, mannitol, ethyl cellulose, sorbitol, starch, sucrose, calcium phosphate, powdered cellulose, silicified microcrystalline cellulose, isomalt, and mixtures thereof. In some embodiments, the filler is silicified microcrystalline cellulose, microcrystalline cellulose, or mixtures thereof. In some other embodiments, the filler is microcrystalline cellulose.

Suitable surfactants include, but are not limited to, sodium lauryl sulfate, sodium dodecyl sulfate, polysorbates (such as Tween 20 and Tween 80), poloxamers (such as Poloxamer 335 and Poloxamer 407), glyceryl monooleate, and mixtures thereof. In some embodiments, the surfactant is sodium lauryl sulfate, sodium dodecyl sulfate, or mixtures thereof. In some embodiments, the surfactant is sodium lauryl sulfate.

Suitable binders include, but are not limited to, polyvinylpyrrolidone, ethyl cellulose, maltose sodium alginate, hydroxypropyl methylcellulose (HPMC), stearic acid, pregelatinized starch, and mixtures thereof. In some embodiments, the binder is HPMC, polyvinylpyrrolidone, or mixtures thereof. In other embodiments, the binder is polyvinylpyrrolidone.

Suitable disintegrants include, but are not limited to, colloidal silicon dioxide, powdered cellulose, calcium silicate, crospovidone, calcium alginate, methyl cellulose, chitosan, carboxy methyl cellulose, croscarmellose sodium, carboxymethyl starch, sodium alginate, sodium starch glycolate, pregelatinized starch, and mixtures thereof. In some embodiments, the disintegrant is croscarmellose sodium, crospovidone, or mixtures thereof. In other embodiments, the disintegrant is croscarmellose sodium.

Suitable lubricants include, but are not limited to, talc, magnesium stearate, sodium stearyl fumarate, glyceryl behenate, hydrogenated vegetable oil, zinc stearate, calcium stearate, sucrose stearate, polyvinyl alcohol, magnesium lauryl sulfate, and mixtures thereof. In some embodiments, the lubricant is magnesium stearate, sodium stearyl fumarate, or mixtures thereof. In other embodiments, the lubricant is sodium stearyl fumarate.

Suitable glidants include, but are not limited to, silicon dioxide, colloidal silicon dioxide, tribasic calcium phosphate, magnesium stearate, magnesium trisilicate, powdered cellulose, talc, starch, and mixtures thereof. In some embodiments, the glidant is talc, colloidal silicon dioxide, or mixtures thereof. In other embodiments, the glidant is colloidal silicon dioxide.

Suitable solvents for the wet granulating step of (a-1) include, but are not limited to, water, ethanol, acetone, and mixtures thereof.

The methods of the invention can be used for preparation of solid pharmaceutical compositions comprising any active ingredient suitable for formulating in solid form with a buffer. Persons having ordinary skill in the art will recognize that an active ingredient having a basic moiety would be best formulated with an acidic buffer, and that an active ingredient having a acidic moiety would be best formulated with a basic buffer. Thus, buffers suitable for use in the present invention include both acidic and basic buffers. For example, in some embodiments, an aqueous solution of the buffer has a pH of less than about 7.0. In other embodiments, an aqueous solution of the buffer has a pH of at least about 7.0. Examples of such buffers are known to persons having ordinary skill in the art and may be found in the Handbook of Pharmaceutical Excipients (5$^{th}$ Edition), APhA publications.

In some embodiments, an aqueous solution of the buffer has a pH of less than about 7.0. In some other embodiments, an aqueous solution of the buffer has a pH of between about 1.0 to about 6.0, or between about 2.0 to about 6.0, or between about 3.0 to about 6.0, or between about 4.0 to about 6.0, or between about 5.0 to about 6.0. Suitable buffers having a pH of less than about 7.0 in aqueous solution include, but are not limited to, disodium citrate, trisodium citrate, sodium acetate, monopotassium phosphate, monosodium phosphate, and mixtures thereof.

In some embodiments, an aqueous solution of the buffer has a pH of at least about 7.0. In some other embodiments, an aqueous solution of the buffer has a pH of between about 8.0 to about 13.0, or between about 8.0 to about 12.0, or between about 8.0 to about 11.0, or between about 8.0 to about 10.0, or between about 8.0 to about 9.0.

Suitable buffers having a pH of at least about 7.0 in aqueous solution include, but are not limited to, sodium bicarbonate, disodium phosphate, dipotassium phosphate, potassium bicarbonate, sodium carbonate, potassium carbonate, and mixtures thereof. In some embodiments, the buffer is sodium bicarbonate, sodium carbonate, or mixtures thereof. In other embodiments, the buffer is sodium bicarbonate.

In some embodiments, the active ingredient contains an acid moiety. In some other embodiments, the active ingredient is a compound of formula (A):

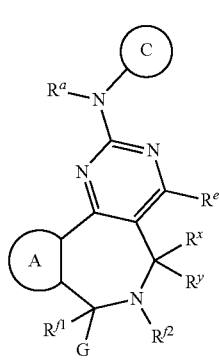

(A)

or a pharmaceutically acceptable salt thereof; wherein:
$R^{f1}$ is hydrogen, or $R^{f1}$ and $R^{f2}$ together form a bond;
$R^{f2}$ is hydrogen, or $R^f$ forms a bond with either $R^{f1}$ or $R^x$;
each of $R^x$ and $R^y$ independently is hydrogen, fluoro, or an optionally substituted $C_{1-6}$ aliphatic; or $R^x$ and $R^y$, taken together with the carbon atom to which they are attached, form an optionally substituted 3- to 6-membered cycloaliphatic ring; or $R^x$ and $R^{f2}$ together form a bond;
G is hydrogen, an optionally substituted aliphatic or Ring B when $R^{f1}$ is hydrogen; and G is hydrogen, —OR, —N($R^4$)$_2$, —SR, an optionally substituted aliphatic, or Ring B when $R^{f1}$ and $R^{f2}$ together form a bond;
Ring A is a substituted or unsubstituted 5- or 6-membered aryl, heteroaryl, cycloaliphatic, or heterocyclyl ring;
Ring B is a substituted or unsubstituted aryl, heteroaryl, heterocyclyl, or cycloaliphatic ring;
Ring C is a substituted or unsubstituted aryl, heteroaryl, heterocyclyl, or cycloaliphatic ring;

$R^a$ is hydrogen, —C(O)R$^1$, —CO$_2$R$^1$, —SO$_2$R$^1$, or a $C_{1-3}$ aliphatic having 0-2 substituents independently selected from R$^3$ or R$^7$;
$R^e$ is hydrogen, —OR$^5$, —N(R$^4$)$_2$, —SRS, —NR$^4$C(O)R$^5$, —NR$^4$C(O)N(R$^4$)$_2$—NR$^4$CO$_2$R$^6$, —N(R$^4$)SO$_2$R$^6$, —N(R$^4$)SO$_2$N(R$^4$)$_2$, or a $C_{1-3}$ aliphatic optionally substituted with R$^3$ or R$^7$;
$R^1$ is $C_{1-6}$ aliphatic or an optionally substituted aryl, heteroaryl, or heterocyclyl group;
each R$^3$ independently is selected from the group consisting of -halo, —OH, —O(C$_{1-3}$alkyl), —CN, —N(R$^4$)$_2$, —C(O)(C$_{1-3}$ alkyl), —CO$_2$H, —CO$_2$(C$_{1-3}$ alkyl), —C(O)NH$_2$, and —C(O)NH(C$_{1-3}$alkyl);
each R$^4$ independently is hydrogen or an optionally substituted aliphatic, aryl, heteroaryl, or heterocyclyl group; or two R$^4$ on the same nitrogen atom, taken together with the nitrogen atom, form an optionally substituted 5- to 6-membered heteroaryl or 4- to 8-membered heterocyclyl ring having, in addition to the nitrogen atom, 0-2 ring heteroatoms selected from N, O, and S;
each R$^5$ independently is hydrogen or an optionally substituted aliphatic, aryl, heteroaryl, or heterocyclyl group;
each R$^6$ independently is an optionally substituted aliphatic or aryl group;
each R$^7$ independently is an optionally substituted aryl, heterocyclyl, or heteroaryl group.

In still a further embodiment, the active ingredient is a compound of formula (I):

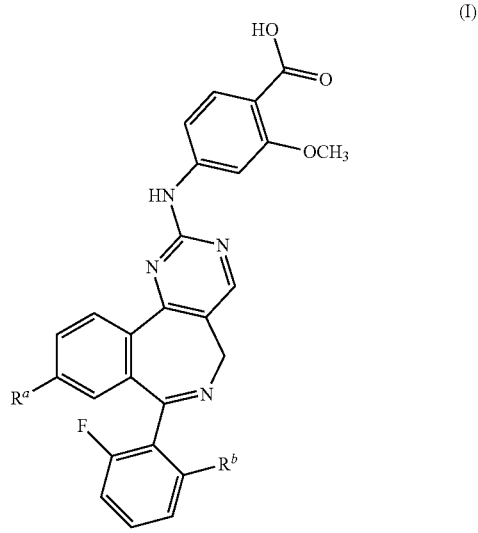

(I)

or a pharmaceutically acceptable salt thereof, wherein:
$R^a$ is selected from the group consisting of $C_{1-3}$ aliphatic, $C_{1-3}$ fluoroaliphatic, —R$^1$, -T-R$^2$, —R$^2$, and -T-R$^2$;
T is a $C_{1-3}$alkylene chain optionally substituted with fluoro;
$R^1$ is an optionally substituted aryl, heteroaryl, or heterocyclyl group;
$R^2$ is selected from the group consisting of halo, —C≡C—R$^3$, —CH=CH—R$^3$, —N(R$^4$)$_2$, and —OR$^5$;
$R^3$ is hydrogen or an optionally substituted aliphatic, aryl, heteroaryl, or heterocyclyl group;

each $R^4$ independently is hydrogen or an optionally substituted aliphatic, aryl, heteroaryl, or heterocyclyl group; or two $R^4$ on the same nitrogen atom, taken together with the nitrogen atom form an optionally substituted 5- to 6-membered heteroaryl or 4- to 8-membered heterocyclyl ring having, in addition to the nitrogen atom, 0-2 ring heteroatoms selected from N, O, and S;

$R^5$ is hydrogen or an optionally substituted aliphatic, aryl, heteroaryl, or heterocyclyl group;

$R^b$ is selected from the group consisting of fluoro, chloro, —CH$_3$, —CF$_3$, —OH, —OCH$_3$, —OCF$_3$, —OCH$_2$CH$_3$, and —OCH$_2$CF$_3$.

Definitions for the substituent groups of the compounds of formula (A) and formula (I) can be found in U.S. Pat. No. 7,572,784 and US Publication No. 2008/0167292, respectively, hereby incorporated by reference in their entirety. Unless otherwise stated, structures depicted herein are also meant to include solvated and hydrated forms of the depicted compounds. Also included within the scope of the invention are compositions comprising pharmaceutically acceptable salts of compounds of formula (A) or formula (I), as well as solvated and hydrated forms of such salts.

If pharmaceutically acceptable salts of the compounds of formula (A) are utilized in the compositions of the invention, the salts preferably are derived from inorganic or organic acids and bases. For reviews of suitable salts, see, e.g., Berge et al, *J. Pharm. Sci.* 66:1-19 (1977) and *Remington: The Science and Practice of Pharmacy,* 20th Ed., ed. A. Gennaro, Lippincott Williams & Wilkins, 2000.

Nonlimiting examples of suitable acid addition salts include the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Suitable base addition salts include, without limitation, ammonium salts, alkali metal salts, such as sodium and potassium salts, alkaline earth metal salts, such as calcium and magnesium salts, salts with organic bases, such as dicyclohexylamine, N-methyl-D-glucamine, t-butylamine, ethylene diamine, ethanolamine, and choline, and salts with amino acids such as arginine, lysine, and so forth. For example, compounds of formula (A), wherein Ring C is substituted with —CO$_2$H may be formulated as a corresponding base addition salt, e.g., a corresponding sodium salt.

If a pharmaceutically acceptable salts of the compounds of formula (I) are utilized in the compositions of the invention, the salts preferably are base addition salts. Suitable base addition salts are as described above for the compounds of formula (A). In some embodiments, the active ingredient is a compound of formula (I), or a sodium or potassium salt thereof.

In some embodiments, the active ingredient is a crystalline form of a compound of formula (A) or formula (I). In some other embodiments, the active ingredient is a crystalline form of a pharmaceutically acceptable salt of a compound of formula (A) or formula (I). Some examples of pharmaceutically acceptable salts of the compounds of formula (A) or formula (I) and crystalline forms thereof can be found in U.S. Pat. No. 7,572,784, US Publication No. 2008/0167292, and U.S. Application No. 61/306,047, filed Feb. 19, 2010, hereby incorporated by reference in their entirety.

In still a further embodiment, the active ingredient is sodium 4-{[9-chloro-7-(2-fluoro-6-methoxyphenyl)-5H-pyrimido[5,4-d][2]benzazepin-2-yl]amino}-2-methoxybenzoate (Compound 1), or a crystalline form thereof. In another embodiment, the active ingredient is sodium 4-{[9-chloro-7-(2-fluoro-6-methoxyphenyl)-5H-pyrimido[5,4-d][2]benzazepin-2-yl]amino}-2-methoxybenzoate (Compound 1) monohydrate. In another embodiment, the active ingredient is sodium 4-{[9-chloro-7-(2-fluoro-6-methoxyphenyl)-5H-pyrimido[5,4-d][2]benzazepin-2-yl]amino}-2-methoxybenzoate (Compound 1) polymorph Form 2, as described in US Publication No. 2008/0167292, and U.S. Application No. 61/306,047, filed Feb. 19, 2010, hereby incorporated by reference in their entirety.

Suitable materials that may be used to film-coat the tablets in step (c-2) include, but are not limited to, Opadry® (Hydroxy propyl methylcellulose PEG) (Colorcon, West Point, Pa.), Opadry® II (Polyvinyl alcohol, PEG, talc, and Titanium dioxide), Opadry® fx, Opadry® amb, and mixtures thereof. In some embodiments, the film-coat material is Opadry®, Opadry® II, or mixtures thereof. In other embodiments, the film-coat material is Opadry® II.

Suitable materials that may be used to enterically coat the tablets in step (c-2) include, but are not limited to, Acryl-EZE® (Methacrylic acid copolymer, talc, SLS, Titanium dioxide, Sodium bicarbonate, Silica, Triethyl Citrate) (Colorcon, West Point, Pa.), cellulose acetate phthalate (CAP), methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), methyl methacrylate-methacrylic acid copolymers, and mixtures thereof.

In some embodiments, the pharmaceutical composition produced after step (a-4) comprises about 1% w/w to about 60% w/w of active ingredient, about 10% w/w to about 80% w/w of buffer, and about 10% w/w to about 80% w/w of filler. In a further embodiment, the pharmaceutical composition comprises from about 2% w/w to about 22% w/w of Compound 1, or a crystalline form thereof. In some embodiments, the pharmaceutical composition comprises from about 3% w/w to about 15% w/w of Compound 1, or a crystalline form thereof. In some other embodiments, the pharmaceutical composition comprises about 13.6% w/w of Compound 1, or a crystalline form thereof.

In some further embodiments, the pharmaceutical composition comprises a sodium bicarbonate buffer, wherein the sodium bicarbonate buffer is present in the amount from about 10% w/w to about 60% w/w. In some embodiments, the sodium bicarbonate buffer is present in the amount from about 20% w/w to about 40% w/w. In some other embodiments, the sodium bicarbonate buffer is present in the amount of about 30% w/w.

In still further embodiments, the pharmaceutical composition comprises a microcrystalline cellulose filler, wherein the microcrystalline cellulose filler is present in the amount from about 27% w/w to about 53% w/w.

In still further embodiments, the bulk composition comprises a sodium stearyl fumarate lubricant, wherein the sodium stearyl fumarate lubricant is present in the amount from about 0% w/w to about 3% w/w.

In still further embodiments, the pharmaceutical composition produced after step (a-4) comprises, about 0% w/w to about 5% w/w of surfactant, about 0% w/w to about 20% w/w of binder, and about 0% w/w to about 20% w/w of disintegrant.

In still further embodiments, about 30% to about 70% of the total amount of the disintegrant is added during step (a-1) and about 30% to about 70% of the total amount of the disintegrant is added during step (a-4).

In another aspect, the present invention provides pharmaceutical compositions. In some embodiments, the pharmaceutical compositions of the invention may be prepared by the methods described herein. In some other embodiments, the pharmaceutical compositions of the invention are bulk compositions.

In one embodiment, the bulk composition comprises an active ingredient, a buffer, and a filler. In another embodiment, the bulk composition comprises an active ingredient, a buffer, a filler, and optionally one or more pharmaceutically acceptable excipients independently selected from the group consisting of a lubricant, a surfactant, a binder, a disintegrant, and a glidant. In yet another embodiment, the bulk composition comprises an active ingredient, a buffer, a filler, a lubricant, a surfactant, a binder, and a disintegrant.

In one embodiment, the bulk composition comprises about 1% w/w to about 60% w/w of active ingredient, about 10% w/w to about 80% w/w of buffer, and about 10% w/w to about 80% w/w of filler. In another embodiment, the bulk composition comprises about 1% w/w to about 60% w/w of active ingredient, about 10% w/w to about 80% w/w of buffer, about 10% w/w to about 80% w/w of filler, about 0% w/w to about 5% w/w of lubricant, about 0% w/w to about 5% w/w of surfactant, about 0% w/w to about 20% w/w of binder, about 0% w/w to about 20% w/w of disintegrant, and about 0% w/w to about 5% w/w of a glidant.

In another embodiment, the bulk composition comprises about 1% w/w to about 30% w/w of active ingredient, about 30% w/w to about 60% w/w of buffer, and about 20% w/w to about 60% w/w of filler, about 1% w/w to about 3% w/w of lubricant, about 0% w/w to about 3% w/w of surfactant, about 0% w/w to about 10% w/w of binder, about 0% w/w to about 15% w/w of disintegrant, and about 0% w/w to about 2% w/w of a glidant.

In another embodiment, the bulk composition comprises about 10% w/w to about 16% w/w of active ingredient, about 28% w/w to about 40% w/w of buffer, about 35% w/w to about 45% w/w of filler, about 1% w/w to about 2% w/w of lubricant, about 1% w/w to about 2% w/w of surfactant, about 3% w/w to about 7% w/w of binder, about 5% w/w to about 10% w/w of disintegrant, and about 0% w/w to about 2% w/w of a glidant.

In another embodiment, the bulk composition comprises about 13.6% w/w of active ingredient, about 30.0% w/w of buffer, and about 40.4% w/w of filler, about 1.0% w/w of lubricant, about 2.0% w/w of surfactant, about 5.0% w/w of binder, and about 8.0% w/w of disintegrant.

Suitable fillers include, but are not limited to, lactose, microcrystalline cellulose, mannitol, ethyl cellulose, sorbitol, starch, sucrose, calcium phosphate, powdered cellulose, silicified microcrystalline cellulose, isomalt, and mixtures thereof. In some embodiments, the filler is silicified microcrystalline cellulose, microcrystalline cellulose, or mixtures thereof. In some other embodiments, the filler is microcrystalline cellulose.

In some embodiments, the filler is present in an amount from about 10% w/w to about 80% w/w. In other embodiments, the filler is present in an amount from about 20% w/w to about 60% w/w, or about 25% w/w to about 55% w/w, or about 30% w/w to about 50% w/w, or about 35% w/w to about 45% w/w. In some embodiments, the filler is present in an amount of about 20% w/w, about 25% w/w, about 30% w/w, about 35% w/w, about 40% w/w, about 45% w/w, about 50% w/w, about 55% w/w, or about 65% w/w In some other embodiments, the filler is present in an amount of about 40.4% w/w.

In some embodiments, the filler comprises a first filler, which is added during step (a-1), and a second filler, which is added during step (a-4), which may be the same or different. In some embodiments, the first filler and the second filler are the same. In some other embodiments, only the first filler is present. In yet some other embodiments, only the second filler is present.

In some embodiments, the first filler, and the second filler are each independently selected from the group consisting of lactose, microcrystalline cellulose, mannitol, ethyl cellulose, sorbitol, starch, sucrose, calcium phosphate, powdered cellulose, silicified microcrystalline cellulose, isomalt, and mixtures thereof. In some other embodiments, the first filler, and the second filler are each independently selected from the group consisting of silicified microcrystalline cellulose, microcrystalline cellulose, or mixtures thereof. In certain particular embodiments, the first filler, and the second filler are both microcrystalline cellulose.

In some embodiments, the first filler and second filler are each present in the same amount, provided that the total amount of filler is no greater than about 80% w/w. In other embodiments, the first filler and second filler are each present in different amounts, provided that the total amount of filler is no greater than about 80% w/w. In some other embodiments, the first filler and second filler are each independently present in an amount from about 0% w/w to about 80% w/w, provided that the total amount of filler is no greater than about 80% w/w. In some other embodiments, the first filler and second filler are each independently present in an amount from about 5% w/w to about 40% w/w. In some other embodiments, the first filler and second filler are each independently present in an amount from about 10% w/w to about 30% w/w. In some other embodiments, the first filler and second filler are each independently present in an amount of about 10% w/w, or about 15% w/w, or about 20% w/w, or about 25% w/w, or about 30%, w/w. In some other embodiments, the first filler and second filler are each independently present in an amount of about 20% w/w.

Suitable surfactants include, but are not limited to, sodium lauryl sulfate, sodium dodecyl sulfate, polysorbates (such as Tween 20 and Tween 80), poloxamers (such as Poloxamer 335 and Poloxamer 407), glyceryl monooleate, and mixtures thereof. In some embodiments, the surfactant is sodium lauryl sulfate, sodium dodecyl sulfate, or mixtures thereof. In some embodiments, the surfactant is sodium lauryl sulfate.

In some embodiments, the surfactant is present in an amount from about 0% w/w to about 5% w/w. In other embodiments, the surfactant is present in an amount from about 0% w/w to about 3% w/w. In other embodiments, the surfactant is present in an amount from about 1% w/w to about 2% w/w. In some other embodiments, the surfactant is present in an amount of about 0.5% w/w, or about 1% w/w, or about 1.5% w/w, or about 2% w/w, or about 2.5% w/w, or about 3% w/w. In some other embodiments, the surfactant is present in an amount of about 2% w/w.

In some embodiments, the surfactant comprises a first surfactant, which is added during step (a-1), and a second surfactant which is added during step (a-4), which may be the same or different. In some embodiments, the first surfactant and the second surfactant are the same. In some other embodiments, only the first surfactant is present. In yet some other embodiments, only the second surfactant is present.

In some embodiments, the first surfactant, and the second surfactant are each independently selected from the group consisting of sodium lauryl sulfate, sodium dodecyl sulfate, polysorbates (such as Tween 20 and Tween 80), poloxamers (such as Poloxamer 335 and Poloxamer 407), glyceryl monooleate, and mixtures thereof. In some embodiments, the surfactant is sodium lauryl sulfate, sodium dodecyl sulfate, or mixtures thereof. In some other embodiments, the first surfactant, and the second surfactant are both sodium lauryl sulfate.

In some embodiments, the first surfactant and second surfactant are each present in the same amount, provided that the total amount of surfactant is no greater than about 5% w/w. In other embodiments, the first surfactant and second surfactant are each present in different amounts, provided that the total amount of surfactant is no greater than about 5% w/w. In some other embodiments, the first surfactant and second surfactant are each independently present in an amount from about 0% w/w to about 5% w/w, provided that the total amount of surfactant is no greater than about 5% w/w. In some other embodiments, the first surfactant and second surfactant are each independently present in an amount of about 0.5% w/w, or about 1% w/w, or about 1.5% w/w, or about 2% w/w, or about 2.5% w/w, or about 3% w/w, provided that the total amount of surfactant is no greater than about 5% w/w. In some other embodiments, the first surfactant and second surfactant are each independently present in an amount of about 1% w/w.

Suitable binders include, but are not limited to, polyvinylpyrrolidone, ethyl cellulose, maltose sodium alginate, hydroxypropyl methylcellulose (HPMC), stearic acid, pregelatinized starch, and mixtures thereof. In some embodiments, the binder is HPMC, polyvinylpyrrolidone, or mixtures thereof. In other embodiments, the binder is polyvinylpyrrolidone.

In some embodiments, the binder is present in an amount from about 0% w/w to about 20% w/w. In other embodiments, the binder is present in an amount from about 0% w/w to about 10% w/w. In some other embodiments, the binder is present in an amount of about 1% w/w, or about 2% w/w, or about 3% w/w, or about 4% w/w, or about 5% w/w, or about 6% w/w, or about 7% w/w, or about 8% w/w, or about 9% w/w, or about 10% w/w. In some other embodiments, the binder is present in an amount from about 1% w/w to about 9% w/w, or about 2% w/w to about 8% w/w, or about 3% w/w to about 7% w/w, or about 4% w/w to about 6% w/w. In some other embodiments, the binder is present in an amount of about 5%.

In some embodiments, the binder comprises a first binder, which is added during step (a-1), and a second binder which is added during step (a-4), which may be the same or different. In some embodiments, the first binder and the second binder are the same. In some other embodiments, only the first binder is present. In yet some other embodiments, only the second binder is present.

In some embodiments, the first binder, and the second binder are each independently selected from the group consisting of polyvinylpyrrolidone, ethyl cellulose, maltose sodium alginate, hydroxypropyl methylcellulose (HPMC), stearic acid, pregelatinized starch, and mixtures thereof. In some embodiments, the first binder, and the second binder are each independently selected from the group consisting of HPMC, polyvinylpyrrolidone, and mixtures thereof. In certain particular embodiments, the first binder, and the second binder are both polyvinylpyrrolidone.

In some embodiments, the first binder and second binder are each present in the same amount, provided that the total amount of binder is no greater than about 20% w/w. In other embodiments, the first binder and second binder are each present in different amounts, provided that the total amount of binder is no greater than about 20% w/w. In some other embodiments, the first binder and second binder are each independently present in an amount from about 0% w/w to about 20% w/w, provided that the total amount of binder is no greater than about 20% w/w. In some other embodiments, the first binder and second binder are each independently present in an amount from about 0% w/w to about 10% w/w. In some other embodiments, the first binder and second binder are each independently present in an amount from about 0% w/w to about 5% w/w. In some other embodiments, the first binder and second binder are each independently present in an amount of about 0.5% w/w, or about 1% w/w, or about 1.5% w/w, or about 2% w/w, or about 2.5% w/w, or about 3% w/w, or about 3.5% w/w, or about 4% w/w, or about 4.5% w/w, or about 5% w/w. In some other embodiments, the first binder and second binder are each independently present in an amount of about 2.5% w/w.

Suitable disintegrants include, but are not limited to, colloidal silicon dioxide, powdered cellulose, calcium silicate, crospovidone, calcium alginate, methyl cellulose, chitosan, carboxy methyl cellulose, croscarmellose sodium, carboxymethyl starch, sodium alginate, sodium starch glycolate, pregelatinized starch, and mixtures thereof. In some embodiments, the disintegrant is croscarmellose sodium, crospovidone, or mixtures thereof. In other embodiments, the disintegrant is croscarmellose sodium.

In some embodiments, the disintegrant is present in an amount from about 0% w/w to about 20% w/w. In other embodiments, the disintegrant is present in an amount from about 0% w/w to about 15% w/w. In some other embodiments the disintegrant is present in an amount from about 1% w/w to about 14% w/w, or from about 2% w/w to about 13% w/w, or from about 3% w/w to about 12% w/w, or from about 4% w/w to about 11% w/w, or from about 5% w/w to about 10% w/w, or from about 6% w/w to about 9% w/w, or from about 7% w/w to about 8% w/w. In some other embodiments, the disintegrant is present in an amount of about 4% w/w, or about 5% w/w, or about 6% w/w, or about 7% w/w, or about 8% w/w, or about 9% w/w, or about 10% w/w, or about 11% w/w, or about 12% w/w. In some other embodiments, the disintegrant is present in an amount of about 8% w/w.

In some embodiments, the disintegrant comprises a first disintegrant, which is added during step (a-1), and a second disintegrant, which is added during step (a-4), which may be the same or different. In some embodiments, the first disintegrant and the second disintegrant are the same. In some other embodiments, only the first disintegrant is present. In yet some other embodiments, only the second disintegrant is present.

In some embodiments, the first disintegrant, and the second disintegrant are each independently selected from the group consisting of colloidal silicon dioxide, powdered cellulose, calcium silicate, crospovidone, calcium alginate, methyl cellulose, chitosan, carboxy methyl cellulose, croscarmellose sodium, carboxymethyl starch, sodium alginate, sodium starch glycolate, pregelatinized starch, and mixtures thereof. In some other embodiments, the first disintegrant, and the second disintegrant are each independently selected from the group consisting of croscarmellose sodium, crospovidone, and mixtures thereof. In certain particular embodiments, the first disintegrant, and the second disintegrant are both croscarmellose sodium.

In some embodiments, the first disintegrant and second disintegrant are each present in the same amount, provided that the total amount of disintegrant is no greater than about 20% w/w. In other embodiments, the first disintegrant and second disintegrant are each present in different amounts, provided that the total amount of disintegrant is no greater than about 20% w/w. In some other embodiments, the first disintegrant and second disintegrant are each independently present in an amount from about 0% w/w to about 20% w/w, provided that the total amount of disintegrant is no greater than about 20% w/w. In some other embodiments, the first disintegrant and second disintegrant are each independently present in an amount from about 0% w/w to about 8% w/w. In some other embodiments, the first disintegrant and second disintegrant are each independently present in an amount of about 1% w/w, or about 2% w/w, or about 3% w/w, or about 4% w/w, or about 5% w/w, or about 6% w/w, or about 7% w/w, or about 8% w/w. In some other embodiments, the first disintegrant and second disintegrant are each independently present in an amount of about 4% w/w.

In some embodiments, the first disintegrant and the second disintegrant each independently comprise about 30% to about 70% of the total amount of disintegrant. In other embodiments, the first disintegrant and the second disintegrant each independently comprise about 40% to about 60% of the total amount of disintegrant. In some other embodiments, the first disintegrant and the second disintegrant each independently comprise about 40%, or about 50%, or about 60% of the total amount of disintegrant. In some other embodiments, the first disintegrant and the second disintegrant each independently comprise about 50% of the total amount of disintegrant.

Suitable lubricants include, but are not limited to, talc, magnesium stearate, sodium stearyl fumarate, glyceryl behenate, hydrogenated vegetable oil, zinc stearate, calcium stearate, sucrose stearate, polyvinyl alcohol, magnesium lauryl sulfate, and mixtures thereof. In some embodiments, the lubricant is magnesium stearate, sodium stearyl fumarate, or mixtures thereof. In other embodiments, the lubricant is sodium stearyl fumarate.

In some embodiments the lubricant is present in an amount from about 0% w/w to about 5% w/w. In some embodiments the lubricant is present in an amount from about 1% w/w to about 3% w/w of lubricant. In some embodiments the lubricant is present in an amount from about 1% w/w to about 2% w/w of lubricant. In some other embodiments, the lubricant is present in an amount from about 0.5% w/w to about 4.5% w/w, or from about 0.5% w/w to about 4% w/w, or from about 0.5% w/w to about 3.5% w/w, or from about 0.5% w/w to about 3% w/w. In other embodiments, the lubricant is present in an amount from about 0% w/w to about 3% w/w. In some other embodiments, the lubricant is present in an amount of about 1% w/w.

Suitable glidants include, but are not limited to, silicon dioxide, colloidal silicon dioxide, tribasic calcium phosphate, magnesium stearate, magnesium trisilicate, powdered cellulose, talc, starch, and mixtures thereof. In some embodiments, the glidant is talc, colloidal silicon dioxide, or mixtures thereof. In other embodiments, the glidant is colloidal silicon dioxide.

In some embodiments, the glidant is present in an amount from about 0% w/w to about 5% w/w. In other embodiments, the glidant is present in an amount from about 0% w/w to about 2% w/w. In other embodiments, the glidant is present in an amount from about 0.3% w/w to about 2% w/w, or about 0.8% w/w to 1.5% w/w. In other embodiments, the glidant is present in an amount of about 0.5% w/w, or about 0.7% w/w, or about 1% w/w, or about 1.2% w/w, or about 1.5% w/w, or about 1.7% w/w, or about 2% w/w. In other embodiments, the glidant is present in an amount of about 1% w/w.

Suitable solvents for the wet granulating step of (a-1) include, but are not limited to, water, ethanol, acetone, and mixtures thereof.

In some embodiments, the amount of solvent present in the wet granulating step of (a-1) is from about 10% w/w to about 50% w/w. In other embodiments the solvent is present in an amount from about 15% w/w to about 40% w/w, or about 28% w/w.

As described above, buffers suitable for use in the present invention include both acidic and basic buffers. For example, in some embodiments, an aqueous solution of the buffer has a pH of less than about 7.0. In other embodiments, an aqueous solution of the buffer has a pH of at least about 7.0. Examples of such buffers are known to persons having ordinary skill in the art and may be found in the *Handbook of Pharmaceutical Excipients* (5$^{th}$ Edition), APhA publications.

In some embodiments, an aqueous solution of the buffer has a pH of less than about 7.0. In some other embodiments, an aqueous solution of the buffer has a pH of between about 1.0 to about 6.0, or between about 2.0 to about 6.0, or between about 3.0 to about 6.0, or between about 4.0 to about 6.0, or between about 5.0 to about 6.0. Suitable buffers having a pH of less than about 7.0 in aqueous solution include, but are not limited to, disodium citrate, trisodium citrate, sodium acetate, monopotassium phosphate, monosodium phosphate, and mixtures thereof.

In some embodiments, an aqueous solution of the buffer has a pH of at least about 7.0. In some other embodiments, an aqueous solution of the buffer has a pH of between about 8.0 to about 13.0, or between about 8.0 to about 12.0, or between about 8.0 to about 11.0, or between about 8.0 to about 10.0, or between about 8.0 to about 9.0.

Suitable buffers having a pH of at least about 7.0 in aqueous solution include, but are not limited to, sodium bicarbonate, disodium phosphate, dipotassium phosphate, potassium bicarbonate, sodium carbonate, potassium carbonate, and mixtures thereof. In some embodiments, the buffer is sodium bicarbonate, sodium carbonate, or mixtures thereof. In other embodiments, the buffer is sodium bicarbonate.

In some embodiments, the buffer is present in an amount from about 10% w/w to about 80% w/w. In other embodiments, the buffer is present in an amount from about 15% w/w to about 60% w/w. In some other embodiments, the buffer is present in an amount from about 20% w/w to about 55% w/w, or from about 22% w/w to about 50% w/w, or from about 25% w/w to about 45% w/w, or from about 28% w/w to about 40% w/w. In some other embodiments, the buffer is present in an amount of about 30% w/w.

In one embodiment of the invention, the pharmaceutical composition prepared by the methods of the invention comprises about 30% w/w of sodium bicarbonate buffer.

In some embodiments, the active ingredient contains an acid moiety, as described above. In some other embodiments, the active ingredient is a compound of formula (A), or a pharmaceutically acceptable salt thereof, as described above. In still a further embodiment, the active ingredient is a compound of formula (I), or a pharmaceutically acceptable salt thereof, as described above.

In some embodiments, the active ingredient is a crystalline form of a compound of formula (A) or formula (I). In some other embodiments, the active ingredient is a crystalline form of a pharmaceutically acceptable salt of a compound of formula (A) or formula (I). Some examples of pharmaceutically acceptable salts of the compounds of formula (A) or formula (I) and crystalline forms thereof can be found in US Publication No. 2008/0167292, and U.S. Application No. 61/306,047, filed Feb. 19, 2010, hereby incorporated by reference in their entirety.

In still a further embodiment, the active ingredient is sodium 4-{[9-chloro-7-(2-fluoro-6-methoxyphenyl)-5H-pyrimido[5,4-d][2]benzazepin-2-yl]amino}-2-methoxybenzoate (Compound 1), or a crystalline form thereof. In another embodiment, the active ingredient is sodium 4-{[9-chloro-7-(2-fluoro-6-methoxyphenyl)-5H-pyrimido[5,4-d][2]benzazepin-2-yl]amino}-2-methoxybenzoate (Compound 1) monohydrate. In another embodiment, the active ingredient is sodium 4-{[9-chloro-7-(2-fluoro-6-methoxyphenyl)-5H-pyrimido[5,4-d][2]benzazepin-2-yl]amino}-2-methoxybenzoate (Compound 1) polymorph Form 2, as described in US Publication No. 2008/0167292, and U.S. Application No. 61/306,047, filed Feb. 19, 2010, hereby incorporated by reference in their entirety.

In some embodiments, the active ingredient is present in the amount from about 1% w/w to about 60% w/w. In some other embodiments, the active ingredient is present in the amount from about 1% w/w to about 30% w/w. In some other embodiments, the active ingredient is present in the amount from about 5% w/w to about 25% w/w, or from about 10% w/w to about 20% w/w, or from about 11% w/w to about 18% w/w, or from about 12% w/w to about 16% w/w. In some other embodiments, the active ingredient is present in the amount of about 10% w/w, or about 11% w/w, or about 12% w/w, or about 13% w/w, or about 14% w/w, or about 15% w/w, or about 16% w/w. In some other embodiments, the active ingredient is present in the amount of about 13.6% w/w.

In another embodiment, the bulk composition comprises about 1% w/w to about 60% w/w of Compound 1, or a crystalline form thereof, about 10% w/w to about 80% w/w of sodium bicarbonate, about 10% w/w to about 80% w/w of microcrystalline cellulose, about 0% w/w to about 5% w/w of sodium stearyl fumarate, about 0% w/w to about 5% w/w of sodium lauryl sulfate, about 0% w/w to about 20% w/w of polyvinylpyrrolidone, and about 0% w/w to about 20% w/w of croscarmellose sodium.

In another embodiment, the bulk composition comprises about 1% w/w to about 30% w/w of Compound 1, or a crystalline form thereof, about 30% w/w to about 60% w/w of sodium bicarbonate, and about 20% w/w to about 60% w/w of microcrystalline cellulose, about 1% w/w to about 3% w/w of sodium stearyl fumarate, about 0% w/w to about 3% w/w of sodium lauryl sulfate, about 0% w/w to about 10% w/w of polyvinylpyrrolidone, and about 0% w/w to about 15% w/w of croscarmellose sodium.

In another embodiment, the bulk composition comprises about 10% w/w to about 16% w/w of Compound 1, or a crystalline form thereof, about 28% w/w to about 40% w/w of sodium bicarbonate, about 35% w/w to about 45% w/w of microcrystalline cellulose, about 1% w/w to about 2% w/w of sodium stearyl fumarate, about 1% w/w to about 2% w/w of sodium lauryl sulfate, about 3% w/w to about 7% w/w of polyvinylpyrrolidone, and about 5% w/w to about 10% w/w of croscarmellose sodium.

In another embodiment, the bulk composition comprises about 13.6% w/w of Compound 1, or a crystalline form thereof, about 30.0% w/w of sodium bicarbonate, and about 40.4% w/w of microcrystalline cellulose, about 1.0% w/w of sodium stearyl fumarate, about 2.0% w/w of sodium lauryl sulfate, about 5.0% w/w of polyvinylpyrrolidone, and about 8.0% w/w of croscarmellose sodium.

In further embodiments, the invention provides pharmaceutical compositions that may be formulated into unit dosage forms. The expression "unit dosage form" as used herein refers to a physically discrete unit of agent appropriate for the subject to be treated. In some embodiments, the unit dosage form is a solid oral pharmaceutical dosage form. Examples of solid oral pharmaceutical dosage forms include, but are not limited to tablets, capsules, pills, powders, and granules. In some embodiments, the solid oral pharmaceutical dosage form is a tablet. In some embodiments, the tablets are film-coated, or enterically coated, or both. In some other embodiments, the tablets are enterically coated.

Suitable excipients, including buffers, fillers, lubricants, surfactants, binders and disintegrants that may be used in the solid oral pharmaceutical dosage forms of the invention are described above.

In some embodiments, the active ingredient of the solid oral pharmaceutical dosage form contains an acid moiety, as described above. In some other embodiments, the active ingredient is a compound of formula (A), a compound of formula (I), or a pharmaceutically acceptable salt of a compound of formula (A) or formula (I), as described above.

In some embodiments, the active ingredient of the solid oral pharmaceutical dosage form is a crystalline form of a compound of formula (A) or formula (I). In some other embodiments, the active ingredient of the solid oral pharmaceutical dosage form is a crystalline form of a pharmaceutically acceptable salt of a compound of formula (A) or formula (I). Some examples of pharmaceutically acceptable salts of the compounds of formula (A) or formula (I) and crystalline forms thereof can be found in US Publication No. 2008/0167292, and U.S. Application No. 61/306,047, filed Feb. 19, 2010, hereby incorporated by reference in their entirety.

In still a further embodiment, the active ingredient of the solid oral pharmaceutical dosage form is sodium 4-{[9-chloro-7-(2-fluoro-6-methoxyphenyl)-5H-pyrimido[5,4-d][2]benzazepin-2-yl]amino}-2-methoxybenzoate (Compound 1), or a crystalline form thereof. In another embodiment, the active ingredient of the solid oral pharmaceutical dosage form is sodium 4-{[9-chloro-7-(2-fluoro-6-methoxyphenyl)-5H-pyrimido[5,4-d][2]benzazepin-2-yl]amino}-2-methoxybenzoate (Compound 1) monohydrate. In another embodiment, the active ingredient of the solid oral pharmaceutical dosage form is sodium 4-{[9-chloro-7-(2-fluoro-6-methoxyphenyl)-5H-pyrimido[5,4-d][2]benzazepin-2-yl]amino}-2-methoxybenzoate (Compound 1) polymorph Form 2, as described in US Publication No. 2008/0167292, and U.S. Application No. 61/306,047, filed Feb. 19, 2010, hereby incorporated by reference in their entirety.

Suitable materials that may be used as film coating include, but are not limited to, Opadry® (Hydroxy propyl methylcellulose PEG) (Colorcon, West Point, Pa.), Opadry® II (Polyvinyl alcohol, PEG, talc, and Titanium dioxide), Opadry® fx, Opadry® amb, and mixtures thereof. In some embodiments, the film-coat material is Opadry®, Opadry® II, or mixtures thereof. In other embodiments, the film-coat material is Opadry® II.

In some embodiments, the film-coat material is present in the solid oral pharmaceutical dosage form in an amount from about 0% w/w to about 10% w/w, wherein the total weight includes all the components of the coated tablet including the coating(s). In other embodiments, the film-coat material is present in the solid oral pharmaceutical dosage form in an amount from about 0% w/w to about 8% w/w, wherein the total weight includes all the components of the coated tablet including the coating(s). In other embodiments, the film-coat material is present in the solid oral pharmaceutical dosage form in an amount from about 0% w/w to about 6% w/w, or about 0.5% w/w to 5.5% w/w, or about 1.0% w/w to 5.0% w/w, or about 1.5% w/w to 4.5% w/w, or about 2.0% w/w to 4.0% w/w, wherein the total weight includes all the components of the coated tablet including the coating(s). In other embodiments, the film-coat material is present in the solid oral pharmaceutical dosage form in an amount of about 3.6% w/w, wherein the total weight includes all the components of the coated tablet including the coating(s).

Suitable materials that may be used as enteric coating include, but are not limited to, Acryl-EZE® (Methacrylic acid copolymer, talc, SLS, Titanium dioxide, Sodium bicarbonate, Silica, Triethyl Citrate) (Colorcon, West Point, Pa.), cellulose acetate phthalate (CAP), methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), methyl methacrylate-methacrylic acid copolymers, and mixtures thereof.

In some embodiments, the enteric-coat material is present in the solid oral pharmaceutical dosage form in an amount from about 0% w/w to about 20% w/w, wherein the total weight includes all the components of the coated tablet including the coating(s). In other embodiments, the enteric-coat material is present in the solid oral pharmaceutical dosage form in an amount from about 0% w/w to about 18% w/w, wherein the total weight includes all the components of the coated tablet including the coating(s). In other embodiments, the enteric-coat material is present in the solid oral pharmaceutical dosage form in an amount from about 0% w/w to about 15% w/w, or about 5% w/w to 13% w/w, or about 7% w/w to about 11% w/w, wherein the total weight includes all the components of the coated tablet including the coating(s). In other embodiments, the enteric-coat material is present in the solid oral pharmaceutical dosage form in an amount of about 9.4% w/w, wherein the total weight includes all the components of the coated tablet including the coating(s).

In another embodiment, the solid oral pharmaceutical dosage form comprises about 1% w/w to about 60% w/w of Compound 1, or a crystalline form thereof, about 10% w/w to about 80% w/w of sodium bicarbonate, about 10% w/w to about 80% w/w of microcrystalline cellulose, about 0% w/w to about 5% w/w of sodium stearyl fumarate, about 0% w/w to about 5% w/w of sodium lauryl sulfate, about 0% w/w to about 20% w/w of polyvinylpyrrolidone, about 0% w/w to about 20% w/w of croscarmellose sodium, about 0% w/w to about 10% w/w of film coating, and about 0% w/w to about 20% w/w of enteric coating.

In another embodiment, the solid oral pharmaceutical dosage form comprises about 1% w/w to about 30% w/w of Compound 1, or a crystalline form thereof, about 30% w/w to about 60% w/w of sodium bicarbonate, and about 20% w/w to about 60% w/w of microcrystalline cellulose, about 1% w/w to about 3% w/w of sodium stearyl fumarate, about 0% w/w to about 3% w/w of sodium lauryl sulfate, about 0% w/w to about 10% w/w of polyvinylpyrrolidone, about 0% w/w to about 15% w/w of croscarmellose sodium, about 0.5% w/w to about 5.5% w/w of film coating, and about 5% w/w to about 13% w/w of enteric coating.

In another embodiment, the solid oral pharmaceutical dosage form comprises about 10% w/w to about 16% w/w of Compound 1, or a crystalline form thereof, about 28% w/w to about 40% w/w of sodium bicarbonate, about 35% w/w to about 45% w/w of microcrystalline cellulose, about 1% w/w to about 2% w/w of sodium stearyl fumarate, about 1% w/w to about 2% w/w of sodium lauryl sulfate, about 3% w/w to about 7% w/w of polyvinylpyrrolidone, about 5% w/w to about 10% w/w of croscarmellose sodium about 2% w/w to about 4% w/w of film coating, and about 7% w/w to about 11% w/w of enteric coating.

In another embodiment, the solid oral pharmaceutical dosage form comprises about 11.9% w/w of Compound 1, or a crystalline form thereof, about 26.1% w/w of sodium bicarbonate, and about 35.1% w/w of microcrystalline cellulose, about 0.9% w/w of sodium stearyl fumarate, about 1.7% w/w of sodium lauryl sulfate, about 4.4% w/w of polyvinylpyrrolidone, about 7.0% w/w of croscarmellose sodium, about 3.6% w/w of Opadry® clear coating, and about 9.4% w/w of Acryl-EZE® white enteric coating, wherein the total weight includes all the components of the coated tablet including the coatings.

The pharmaceutical compositions of the invention comprising compounds of formula (A), or pharmaceutically acceptable salts thereof, compounds of formula (I), or pharmaceutically acceptable salts thereof, and Compound 1, or crystalline forms thereof are particularly useful in therapeutic applications relating to mitotic kinase mediated diseases, disorders or conditions, particularly Aurora kinase mediated diseases, disorders or conditions. Inhibiting mitotic kinase activity may serve to treat a number of diseases, involving cell survival, proliferation, and migration, including cancer, as well as other cell-proliferative diseases.

One aspect of the invention, therefore, provides methods for treating Aurora kinase-mediated disorders by administering a therapeutically effective amount of the pharmaceutical composition of the invention. As used herein, the term "Aurora kinase-mediated disorder" includes any disorder, disease or condition which is caused or characterized by an increase in Aurora kinase expression or activity, or which requires Aurora kinase activity. The term "Aurora kinase-mediated disorder" also includes any disorder, disease or condition in which inhibition of Aurora kinase activity is beneficial. Aurora kinase-mediated disorders include proliferative disorders. Non-limiting examples of proliferative disorders include chronic inflammatory proliferative disorders, e.g., psoriasis and rheumatoid arthritis; proliferative ocular disorders, e.g., diabetic retinopathy; benign proliferative disorders, e.g., hemangiomas; and cancer. Non-limiting examples of cancer include colorectal cancer, ovarian cancer, breast cancer, gastric cancer, prostate cancer, and pancreatic cancer.

The physical and chemical stability of the oral pharmaceutical dosage form may be tested in a conventional manner, for example, the measurement of dissolution or disintegration time, or moisture content, or assay for the active ingredient or degradation products after storage at different temperatures for different lengths of time.

The pharmaceutical compositions, prepared according to the method of the present invention, may be administered using any amount effective for treating the disease. The exact amount required will vary from subject to subject, depending on the species, age, and general condition of the subject, the severity of the infection, the particular active ingredient, its mode of administration, and the like. The pharmaceutical compositions are preferably formulated in an oral pharmaceutical unit dosage form for ease of administration and uniformity of dosage. The expression "unit dosage form" as used herein refers to a physically discrete unit of agent appropriate for the subject to be treated. It will be understood, however, that the total daily usage of the pharmaceutical compositions of the present invention will be decided by the attending physician within the scope of sound medical judgment. The specific effective dose level for any particular subject will depend upon a variety of factors including the disease being treated and the severity of the disease; the activity of the specific compound employed; the specific composition employed; the age, body weight, general health, sex and diet of the subject; the time of administration, and rate of excretion of the specific compound employed; the duration of the treatment; drugs used in combination or coincidental with the specific compound employed, and like factors well known in the medical arts.

In some embodiments the unit dosage form comprises about 1 mg to about 250 mg of active ingredient. In some other embodiments the unit dosage form comprises about 5 mg to about 200 mg of active ingredient. In some other embodiments the unit dosage form comprises about 10 mg to about 150 mg of active ingredient. In still some other embodiments the unit dosage form comprises about 10 mg to about 100 mg of active ingredient.

In order that this invention be more fully understood, the following preparative examples are set forth. These examples illustrate how to make or test specific compositions, and are not to be construed as limiting the scope of the invention in any way.

EXAMPLES

Sodium 4-{[9-chloro-7-(2-fluoro-6-methoxyphenyl)-5H-pyrimido[5,4-d][2]benzazepin-2-yl]amino}-2-methoxybenzoate (Compound 1), and crystalline forms thereof may be prepared according to synthetic methods described in US Publication No. 2008/0167292 or U.S. Application No. 61/306,047, filed Feb. 19, 2010, hereby incorporated by reference in its entirety. Where Compound 1 is used in the examples below, the term will be understood to refer to Compound 1, or a crystalline form thereof.

Examples of pharmaceutical compositions that may be prepared using the methods of the present invention are shown in the examples below.

Example 1

The pharmaceutical composition is shown below in Table 1

TABLE 1

| Pharmaceutical composition | | |
|---|---|---|
| Material | Function | Composition (w/w %) |
| Compound 1 | Drug Substance | 3.6 |
| Sodium Lauryl Sulfate | Surfactant | 2.0 |
| Microcrystalline Cellulose | Filler | 50.4 |
| Polyvinylpyrrolidone | Binder | 5.0 |
| Croscarmellose Sodium | Disintegrant (intragranular) | 5.0 |

TABLE 1-continued

| Pharmaceutical composition | | |
|---|---|---|
| Material | Function | Composition (w/w %) |
| Sodium Bicarbonate | Buffer | 30.0 |
| Croscarmellose Sodium | Disintegrant (extragranular) | 3.0 |
| Sodium Stearyl Fumarate | Lubricant | 1.0 |

Example 2

The pharmaceutical composition is shown below in Table 2

TABLE 2

| Pharmaceutical composition | | |
|---|---|---|
| Material | Function | Composition (w/w %) |
| Compound 1 | Drug Substance | 2.0 |
| Sodium Lauryl Sulfate | Surfactant | 1.1 |
| Microcrystalline Cellulose | Filler | 27.5 |
| Polyvinylpyrrolidone | Binder | 2.7 |
| Croscarmellose Sodium | Disintegrant (intragranular) | 2.7 |
| Sodium Bicarbonate | Buffer | 60.0 |
| Croscarmellose Sodium | Disintegrant (extragranular) | 3.0 |
| Sodium Stearyl Fumarate | Lubricant | 1.0 |

Example 3

The pharmaceutical composition is shown below in Table 3

TABLE 3

| Pharmaceutical composition | | |
|---|---|---|
| Material | Function | Composition (w/w %) |
| Compound 1 | Drug Substance | 21.9 |
| Sodium Lauryl Sulfate | Surfactant | 2.0 |
| Microcrystalline Cellulose | Filler | 33.6 |
| Polyvinylpyrrolidone | Binder | 1.5 |
| Croscarmellose Sodium | Disintegrant (intragranular) | 5.0 |
| Sodium Bicarbonate | Buffer | 30.0 |
| Croscarmellose Sodium | Disintegrant (extragranular) | 5.0 |
| Sodium Stearyl Fumarate | Lubricant | 1.0 |

Example 4

A 1.0 kg batch granulation was manufactured by the following process Compound 1 (0.06 kg) was screened and blended with Microcrystalline Cellulose (0.79 kg) in a Diosna P1-6 high shear wet granulator. Polyvinylpyrrolidone (0.08 kg) and Croscarmellose Sodium (0.08 kg) were screened and added to the granulator. The granulating liquid (water) was sprayed at a predetermined spray rate of 50 g/minute using a peristaltic pump. Once the end point was reached with an approximate moisture content of 38.5% of the wet granulated material, the resulting wet granules were screened and subsequently dried using a GPCG-1 fluid bed dryer. The resulting dried granules were screened and weighed. Based on the weight obtained, a calculation was performed to determine the appropriate amount of extragranular components. Sodium Bicarbonate (30% w/w), Croscarmellose Sodium (3% w/w) and Sodium Stearyl Fumarate (1% w/w) were then blended with the screened, dried granules to give a batch with composition as shown in Table 4.

TABLE 4

Pharmaceutical composition

| Material | Function | Composition (w/w %) |
|---|---|---|
| Compound 1 | Drug Substance | 3.6 |
| Microcrystalline Cellulose | Filler | 52.4 |
| Polyvinylpyrrolidone | Binder | 5.0 |
| Croscarmellose Sodium | Disintegrant (intragranular) | 5.0 |
| Sodium Bicarbonate | Buffer | 30.0 |
| Croscarmellose Sodium | Disintegrant (extragranular) | 3.0 |
| Sodium Stearyl Fumarate | Lubricant | 1.0 |

Example 5

A 0.65 kg batch granulation was manufactured by the following process Compound 1 (0.13 kg) was screened and blended with Microcrystalline Cellulose (0.40 kg) in a Diosna P1-6 high shear wet granulator. Sodium Lauryl Sulfate (0.02 kg), Polyvinylpyrrolidone (0.05 kg), and Croscarmellose Sodium (0.05 kg) were screened and added to the granulator. The granulating liquid (water) was sprayed at a predetermined spray rate of 35 g/minute using a peristaltic pump. Once the end point was reached with an approximate moisture content of 37.5% of the wet granulated material, the resulting wet granules were screened subsequently dried using a GPCG-1 fluid bed dryer. The resulting dried granules were screened and weighed. Based on the weight obtained, a calculation was performed to determine the appropriate amount of extra-granular components. Sodium Bicarbonate (30% w/w), Croscarmellose Sodium (3% w/w), and Sodium Stearyl Fumarate (1% w/w) were then blended with the screened, dried granules to give a batch with a composition as shown in Table 5.

TABLE 5

Pharmaceutical composition

| Material | Function | Composition (w/w %) |
|---|---|---|
| Compound 1 | Drug Substance | 13.6 |
| Sodium Lauryl Sulfate | Surfactant | 2.0 |
| Microcrystalline Cellulose | Filler | 40.4 |
| Polyvinylpyrrolidone | Binder | 5.0 |
| Croscarmellose Sodium | Disintegrant (intragranular) | 5.0 |
| Sodium Bicarbonate | Buffer | 30.0 |
| Croscarmellose Sodium | Disintegrant (extragranular) | 3.0 |
| Sodium Stearyl Fumarate | Lubricant | 1.0 |

Example 6

A 4.8 kg batch granulation was manufactured by the following process Compound 1 (0.64 kg) was screened through 14 mesh screen and blended with Microcrystalline Cellulose (1.95 kg), Sodium Lauryl Sulfate (0.1 kg), Polyvinylpyrrolidone (0.24 kg), and Croscarmellose Sodium (0.24 kg) in a PMA25/65 high shear wet granulator. Purified water was sprayed at a predetermined spray rate of 180-235 g/minute using a peristaltic pump. A total of 1 kg of purified water was sprayed in this process. Once the end point was reached with an approximate moisture content of 25% of the wet granulated material, the resulting wet granules were screened subsequently dried using a GPCG-1 fluid bed dryer. The resulting dried granules were screened and weighed. Based on the weight obtained, a calculation was performed to determine the appropriate amount of extra-granular components. Sodium Bicarbonate (30% w/w), Croscarmellose Sodium (3% w/w), and Sodium Stearyl Fumarate (1% w/w) were then blended with the screened, dried granules to give a batch with a composition as shown in Table 5.

Example 7

A 4.8 kg batch granulation was manufactured by the following process Compound 1 (0.64 kg) was screened through 14 mesh screen and blended with Microcrystalline Cellulose (1.95 kg), Sodium Lauryl Sulfate (0.1 kg), Polyvinylpyrrolidone (0.24 kg), and Croscarmellose Sodium (0.24 kg) in a PMA25/65 high shear wet granulator. Purified water was sprayed at a predetermined spray rate of 242 g/minute using a peristaltic pump. A total of 0.8 kg of purified water was sprayed in this process. Wet massing was performed for 2 minutes after spraying the water in this example. Once the end point was reached with an approximate moisture content of 20% of the wet granulated material, the resulting wet granules were screened subsequently dried using a GPCG-1 fluid bed dryer. The resulting dried granules were screened and weighed. Based on the weight obtained, a calculation was performed to determine the appropriate amount of extra-granular components. Sodium Bicarbonate (30% w/w), Croscarmellose Sodium (3% w/w), and Sodium Stearyl Fumarate (1% w/w) were then blended with the screened, dried granules to give a batch with a composition as shown in Table 5.

Example 8

A 4.8 kg batch granulation was manufactured by the following process Compound 1 (0.64 kg) was screened through 14 mesh screen and blended with Microcrystalline Cellulose (1.95 kg), Sodium Lauryl Sulfate (0.1 kg), Polyvinylpyrrolidone (0.24 kg), and Croscarmellose Sodium (0.24 kg) in a PMA25/65 high shear wet granulator. Purified water was sprayed at a predetermined spray rate of 200 g/minute to 254 g/minute using a peristaltic pump. A total of 0.8 kg of purified water was sprayed in this process. Once the end point was reached with an approximate moisture content of 20% of the wet granulated material, the resulting wet granules were screened and subsequently dried using a GPCG-1 fluid bed dryer. The resulting dried granules were screened and weighed. Based on the weight obtained, a calculation was performed to determine the appropriate amount of extra-granular components. Sodium Bicarbonate (30% w/w), Croscarmellose Sodium (3% w/w), and Sodium Stearyl Fumarate (1% w/w) were then blended with the screened, dried granules to give a batch with a composition as shown in Table 5.

Example 9

The resulting final blended granules from Example 5 were loaded into a Piccola 10 station tablet press with 7/32" standard round concave tooling. The granules were compressed to manufacture tablets having a total weight of 80 mg per tablet (10 mg dose of Compound 1). The resulting tablets were coated with a first coat of Opadry® Clear Coating followed by a second coat of Acryl-EZE® White Enteric Coating using a Vector LDCS perforated pan coater. The composition of the resulting enterically coated tablets is shown below in Table 6. The resulting final blended granules from Example 5 may also be used to form the tablet compositions shown below in Tables 7 and 8.

TABLE 6

Tablet composition

| Material | Function | mg/Tablet |
|---|---|---|
| Compound 1 | Drug Substance | 10.9 |
| Sodium Lauryl Sulfate | Surfactant | 1.6 |
| Microcrystalline Cellulose | Filler | 32.3 |
| Polyvinylpyrrolidone | Binder | 4.0 |
| Croscarmellose Sodium | Disintegrant (intragranular) | 4.0 |
| Sodium Bicarbonate | Buffer | 24.0 |
| Croscarmellose Sodium | Disintegrant (extragranular) | 2.4 |
| Sodium Stearyl Fumarate | Lubricant | 0.8 |
| Total Core Tablet Weight (mg) | | 80.0 |
| Opadry ® Clear Coating | Film Coating | 3.3 |
| Acryl-EZE ® White | Enteric Coating | 8.6 |
| Enteric Coating Total Tablet Weight Including Coatings (mg) | | 91.9 |

Example 10

The composition of the tablet is shown below in Table 7

TABLE 7

Tablet composition

| Material | Function | mg/Tablet |
|---|---|---|
| Compound 1 | Drug Substance | 54.5 |
| Sodium Lauryl Sulfate | Surfactant | 8.0 |
| Microcrystalline Cellulose | Filler | 161.5 |
| Polyvinylpyrrolidone | Binder | 20.0 |
| Croscarmellose Sodium | Disintegrant (intragranular) | 20.0 |
| Sodium Bicarbonate | Buffer | 120.0 |
| Croscarmellose Sodium | Disintegrant (extragranular) | 12.0 |
| Sodium Stearyl Fumarate | Lubricant | 4.0 |
| Total Core Tablet Weight (mg) | | 400.0 |
| Opadry ® Clear Coating | Film Coating | 16.8 |
| Acryl-EZE ® White | Enteric Coating | 43.8 |
| Enteric Coating Total Core Tablet Weight Including Coatings (mg) | | 460.6 |

Example 11

The composition of the tablet is shown below in Table 8

TABLE 8

Tablet composition

| Material | Function | mg/Tablet |
|---|---|---|
| Compound 1 | Drug Substance | 109.0 |
| Sodium Lauryl Sulfate | Surfactant | 16.0 |
| Microcrystalline Cellulose | Filler | 323.0 |
| Polyvinylpyrrolidone | Binder | 40.0 |
| Croscarmellose Sodium | Disintegrant (intragranular) | 40.0 |
| Sodium Bicarbonate | Buffer | 240.0 |
| Croscarmellose Sodium | Disintegrant (extragranular) | 24.0 |
| Sodium Stearyl Fumarate | Lubricant | 8.0 |
| Total Tablet Weight (mg) | | 800.0 |
| Opadry ® Clear Coating | Film Coating | 33.0 |
| Acryl-EZE ® White | Enteric Coating | 86.0 |
| Enteric Coating Total Core Tablet Weight Including Coatings (mg) | | 919.0 |

Example 12

A 1.0 kg batch granulation was manufactured by the following process Compound 1 (0.04 kg) was screened and blended with Microcrystalline Cellulose (0.55 kg), Sodium Bicarbonate (0.32 kg) and Croscarmellose Sodium (0.05 kg) in a 4 quart PK blender. The blended mixture was then transferred into a GPCG-1 fluid bed granulator. Polyvinylpyrrolidone (0.05 kg) was mixed with Water (0.3 kg) to make up a binder solution. The binder solution was sprayed at a predetermined spray rate of 21 g/minute using a peristaltic pump. Once the binder solution was all sprayed into the GPCG-1 fluid bed granulator, the drying process continued in the GPCG-1 fluid bed granulator until a predetermined product and exhaust temperature were obtained. The resulting dried granules were screened and weighed. Based on the weight obtained, a calculation was performed to determine the appropriate amount of extra-granular components. Croscarmellose Sodium (3% w/w), and Sodium Stearyl Fumarate (1% w/w) were then blended with the screened, dried granules to give a batch with composition as shown in Table 9.

TABLE 9

Pharmaceutical composition

| Material | Function | Composition (w/w %) |
|---|---|---|
| Compound 1 | Drug Substance | 3.6 |
| Microcrystalline Cellulose | Filler | 52.4 |
| Polyvinylpyrrolidone | Binder | 5.0 |
| Croscarmellose Sodium | Disintegrant (intragranular) | 5.0 |
| Sodium Bicarbonate | Buffer | 30.0 |
| Croscarmellose Sodium | Disintegrant (extragranular) | 3.0 |
| Sodium Stearyl Fumarate | Lubricant | 1.0 |

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

What is claimed is:

1. A method of preparing a pharmaceutical composition comprising the steps of:
    (a-1) wet granulating at least one active ingredient that is the compound 4-{[9-chloro-7-(2-fluoro-6-methoxyphenyl)-5H-pyrimido[5,4-d][2]benzazepin-2-yl]amino}-2-methoxybenzoic acid or a pharmaceutically acceptable salt thereof, or a crystalline form thereof, and optionally one or more pharmaceutically acceptable excipients independently selected from the group consisting of surfactants, binders, and disintegrants in the presence of a suitable solvent to form a wet mixture;

(a-2) drying the wet mixture from step (a-1), to form dried granules;

(a-3) milling the dried granules from step (a-2), to form milled granules; and (a-4) blending the milled granules from step (a-3) with a buffer and optionally one or more pharmaceutically acceptable excipients independently selected from the group consisting of surfactants, binders, disintegrants, lubricants and glidants;

wherein a filler is added during step (a-1), during step (a-4), or during both steps (a-1) and (a-4).

2. The method of claim 1, wherein the method further comprises the step of (b-1) loading the resulting mixture from step (a-4) into a capsule.

3. The method of claim 1, wherein a lubricant is added during step (a-4), and wherein the method further comprises the step of (c-1) tableting the resulting mixture from step (a-4) to form a tablet.

4. The method of claim 3, wherein the method further comprises the step of (c-2) coating the tablet resulting from step (c-1).

5. The method of claim 4, wherein the (c-2) coating step comprises film-coating and enterically coating the tablet resulting from step (c-1).

6. The method of claim 1, wherein the wet granulating step is preceded by step (a-0) dry blending at least one active ingredient that is the compound 4-{[9-chloro-7-(2-fluoro-6-methoxyphenyl)-5H-pyrimido[5,4-d][2]benzazepin-2-yl]amino}-2-methoxybenzoic acid or a pharmaceutically acceptable salt thereof, or a crystalline form thereof, and optionally one or more pharmaceutically acceptable excipients independently selected from the group consisting of surfactants, binders, disintegrants, and fillers.

7. The method of claim 1, wherein the filler is lactose, microcrystalline cellulose, mannitol, ethyl cellulose, sorbitol, starch, sucrose, calcium phosphate, powdered cellulose, silicified microcrystalline cellulose or isomalt.

8. The method of claim 1, wherein the surfactant of step (a-1) or step (a-4) is sodium lauryl sulfate, sodium dodecyl sulfate, polysorbates, poloxamers or glyceryl monooleate.

9. The method of claim 1, wherein the binder of step (a-1) or step (a-4) is polyvinylpyrrolidone, ethyl cellulose, maltose, sodium alginate, hydroxypropyl methylcellulose, stearic acid or pregelatinized starch.

10. The method of claim 1, wherein the disintegrant of step (a-1) and/or step (a-4) is colloidal silicon dioxide, powdered cellulose, calcium silicate, crospovidone, calcium alginate, methyl cellulose, chitosan, carboxy methyl cellulose, croscarmellose sodium, carboxymethyl starch, sodium alginate, sodium starch glycolate or pregelatinized starch.

11. The method of claim 1, wherein the lubricant is talc, magnesium stearate, sodium stearyl fumarate, glyceryl behenate, hydrogenated vegetable oil, zinc stearate, calcium stearate, sucrose stearate, polyvinyl alcohol or magnesium lauryl sulfate.

12. The method of claim 1, wherein the solvent of step (a-1) is water, ethanol or acetone.

13. The method of claim 1, wherein the buffer is sodium bicarbonate, monosodium phosphate, disodium phosphate, monopotassium phosphate, dipotassium phosphate, potassium bicarbonate, sodium carbonate or potassium carbonate.

14. The method of claim 13, wherein the buffer is sodium bicarbonate.

15. The method of claim 14, wherein the sodium bicarbonate buffer is present in an amount from about 20% w/w to about 40% w/w.

16. The method of claim 1, wherein the active ingredient is sodium 4 {[9-chloro-7-(2-fluoro-6-methoxyphenyl)-5H-pyrimido[5,4-d][2]benzazepin-2-yl]amino}-2-methoxybenzoate.

17. The method of claim 16, wherein the active ingredient sodium 4 {[9-chloro-7-(2-fluoro-6-methoxyphenyl)-5H-pyrimido[5,4-d][2]benzazepin-2-yl]amino}-2-methoxybenzoate is present in an amount from about 1% w/w to about 60% w/w.

18. The method of claim 17, wherein the active ingredient sodium 4 {[9-chloro-7-(2-fluoro-6-methoxyphenyl)-5H-pyrimido[5,4-d][2]benzazepin-2-yl]amino}-2-methoxybenzoate is present in an amount from about 10% w/w to about 16% w/w.

19. The method of claim 7, wherein the filler is microcrystalline cellulose.

20. The method of claim 8, wherein the surfactant of step (a-1) or step (a 4) is sodium lauryl sulfate.

21. The method of claim 9, wherein the binder of step (a-1) or step (a-4) is polyvinylpyrrolidone.

22. The method of claim 10, wherein the disintegrant of step (a-1) and/or step (a-4) is croscarmellose sodium.

23. The method of claim 11, wherein the lubricant is sodium stearyl fumarate.

24. The method of claim 5, wherein the film coat is present in the amount from about 0.5% w/w to about 5.5% w/w, and the enteric coat is present in the amount from about 5% w/w to about 13% w/w.

* * * * *